United States Patent
McGeorge et al.

(10) Patent No.: US 6,475,433 B2
(45) Date of Patent: Nov. 5, 2002

(54) METHOD AND APPARATUS FOR VERIFYING ULTRAVIOLET STERILIZATION

(75) Inventors: Gram J. McGeorge, Spring Lake; Philip DeVries, Holland, both of MI (US)

(73) Assignee: EBW Electronics, Inc., Holland, MI (US)

( * ) Notice: Subject to any disclaimer, the term of this patent is extended or adjusted under 35 U.S.C. 154(b) by 0 days.

(21) Appl. No.: 09/761,225

(22) Filed: Jan. 16, 2001

(65) Prior Publication Data

US 2001/0048891 A1 Dec. 6, 2001

Related U.S. Application Data

(60) Provisional application No. 60/178,921, filed on Feb. 1, 2000, and provisional application No. 60/189,770, filed on Mar. 16, 2000.

(51) Int. Cl.[7] .............................. A61L 2/00; C02F 1/48; G01J 1/42
(52) U.S. Cl. ........................... 422/24; 422/23; 422/905; 210/748; 250/372; 250/432 R; 250/433
(58) Field of Search .................... 422/24, 23, 905; 210/748, 372, 432 R, 433

(56) References Cited

U.S. PATENT DOCUMENTS

| | | | |
|---|---|---|---|
| 4,344,918 A | * 8/1982 | Takahashi | 422/80 |
| 4,752,401 A | * 6/1988 | Bodenstein | 210/746 |
| 4,788,433 A | 11/1988 | Wright | 250/474.1 |
| 4,896,042 A | * 1/1990 | Humphreys | 250/435 |
| 5,028,792 A | 7/1991 | Mullins | 250/474.1 |
| 5,436,115 A | 7/1995 | Mullis | 430/338 |
| 5,581,090 A | * 12/1996 | Goudjil | 250/474.1 |
| 5,696,381 A | 12/1997 | Quintern | 250/472.1 |
| 5,900,212 A | 5/1999 | Maiden et al. | 422/24 |
| 5,914,197 A | 6/1999 | Goudjil | 428/537.5 |

* cited by examiner

Primary Examiner—Terrence R. Till
Assistant Examiner—Imad Soubra
(74) Attorney, Agent, or Firm—King & Jovanovic, PLC

(57) ABSTRACT

A photochromic material which undergoes a change in appearance when exposed to ultraviolet (UV) radiation in the UVC band provides a visual indication of the degree of sterilization achieved by a UV emitting device. The photochromic material is placed either on the UV source or in or adjacent the sample being sterilized. The photochromic material is formulated to undergo a certain degree of change in appearance when it has been exposed to a level of UV which corresponds to effective sterilization of the sample being sterilized. An optional reference card bears a color or opacity reference for comparison with the exposed photochromic material.

4 Claims, 3 Drawing Sheets

METHOD AND APPARATUS FOR VERIFYING ULTRAVIOLET STERILIZATION

CROSS-REFERENCE TO RELATED APPLICATIONS

This application claims the benefit of U.S. Provisional applications Ser. No. 60/178,921, filed Feb. 1, 2000; and Ser. No. 60/189,770, filed Mar. 16, 2000.

BACKGROUND OF THE INVENTION

The present invention relates generally to a process and apparatus for sterilizing a desired material; and more particularly to such a process and apparatus which utilizes ultraviolet radiation to achieve a desired degree of sterilization.

It is well known that ultraviolet radiation (UV) in the UVC band (100 to 290 nm wavelength can be used to kill bacteria and other biological contaminants present on surfaces, in liquids, or in gases. A certain minimum amount of radiant energy is required to kill a given population of contaminants, this minimum amount depending on several factors including the concentration of contaminants on or in the material to be sterilized.

Various appliances are available which generate UV radiation to sterilize surfaces or liquids. These include air purifiers, water purifiers, medical instrument sterilizers, and other devices. Some of these devices are of the flow-through type, in which a stream of liquid or gas passes through the device, and while inside, is exposed to UV radiation. Examples of hand held sterilization appliances are disclosed in U.S. Pat. No. 4,896,042 and U.S. Pat. No. 5,900,212.

When using a UV sterilization appliance, there is often no reliable way to determine whether the amount of UV energy being emitted by the appliance is sufficient for sterilization. Many different faults may occur in such appliances which could diminish the amount of energy output sufficiently to prevent complete sterilization. Such faults may include old or defective UV sources, defective drive circuits, inadequate power supplies, or low ambient temperatures.

Thus, it is an object of the present invention to provide a method and apparatus for accurately determining whether a material has received an adequate amount of UV exposure to achieve proper sterilization. It is a further object of the present invention to provide such a method and apparatus which is facile and cost effective to use. Still further, it is an object of the present invention to provide such a method and apparatus having a sterilization monitoring means which may be disposable and/or reusable.

SUMMARY OF THE INVENTION

The present invention addresses and solves the above-mentioned problems and meets the enumerated objects and advantages, as well as others not enumerated, by providing an apparatus for sterilizing a desired material, the apparatus comprising an ultraviolet (UV) radiation generator for generating ultraviolet radiation in the UVC range, wherein the generator is adapted to direct the ultraviolet radiation at the desired material. The apparatus further comprises means for monitoring the desired material to detect an amount of cumulative exposure thereto by the ultraviolet radiation in the UVC range. The monitoring means may comprise an indicator strip adapted to be positioned adjacent at least one of the desired material and the generator. The indicator strip may have a photochromic material disposed thereon, wherein the photochromic material changes in appearance in proportion to intensity and duration of exposure to the ultraviolet radiation in the UVC range.

A method for sterilizing an aqueous solution according to the present invention comprises the steps of: directing ultraviolet radiation (UV) in the range from about 200 nm to about 290 nm toward the aqueous solution; and monitoring the aqueous solution to detect an amount of cumulative exposure thereto by the ultraviolet radiation. The monitoring step may be performed by an indicator strip as described above.

BRIEF DESCRIPTION OF THE DRAWINGS

Other objects, features and advantages of the present invention will become apparent by reference to the following detailed description and drawings, in which.

DETAILED DESCRIPTION OF THE PREFERRED EMBODIMENTS

Figure 1:
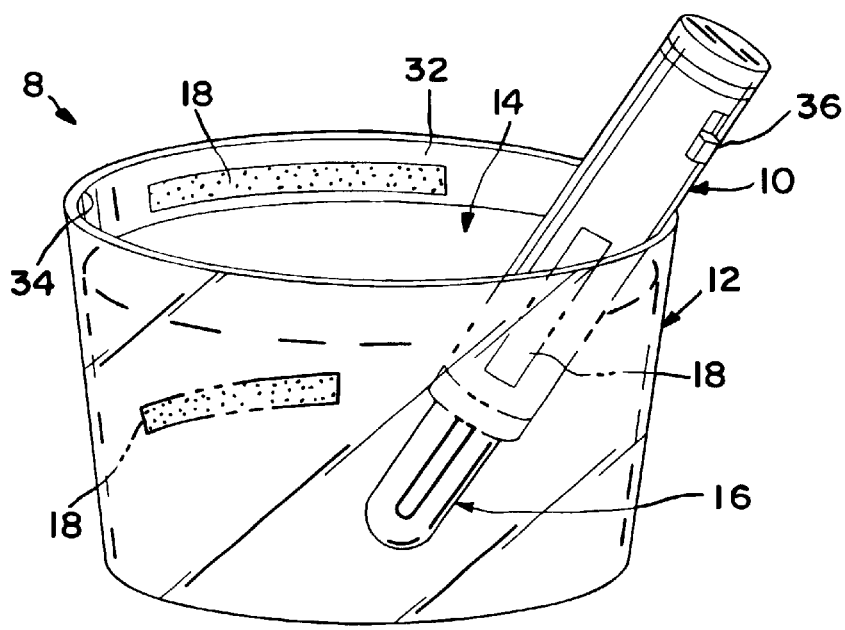
FIG. 1 is a perspective view of a sterilization apparatus according to the present invention, showing the indicator strip on the reservoir, in phantom on the UV generator, and in phantom in the reservoir within the fluid to be sterilized.

Referring now to FIG. 1, the apparatus for sterilizing a desired material 14 is designated generally as 8. Apparatus 8 comprises an ultraviolet (UV) radiation generator 10 for generating ultraviolet radiation in the UVC range, wherein the generator 10 is adapted to direct the ultraviolet radiation at the desired material 14. It is to be understood that any suitable UV radiation generator 10 may be used; however, in the preferred embodiment, a hand held ultraviolet radiation generator 10 similar to that disclosed in U.S. Pat. No. 5,900,212 is used. Generator 10 includes an ultraviolet (UV) radiation emitting bulb 16. Generator 10 is shown to be portable and held by hand H in FIG. 5. Preferably, UV generator 10, 10' is suitable for immersion in water. As disclosed in the '212 patent, the generator 10 is activated via switch 36 and stirred around in fluid 14 for a length of time sufficient to sterilize the fluid 14.

It is to be understood that the desired material 14 may be any material which may be sterilized by UVC radiation. In the preferred embodiment, this material 14 is a sterilizable liquid, preferably an aqueous solution; and more preferably water.

It is to be further understood that the term "sterilize," "sterilizable," and the like as used herein is not meant to imply complete elimination of bacteria, viruses and algae. Rather, the term(s) as used herein are contemplated as encompassing the disinfection of the desired material, ie. elimination of enough bacteria, viruses, algae and/or other contaminants so as to make the desired material safe for use and/or consumption.

Apparatus 8 further comprises means for monitoring the desired material 14 to detect an amount of cumulative exposure thereto by the ultraviolet radiation in the UVC range. The monitoring means may comprise an indicator strip 18 adapted to be positioned adjacent the desired material 14 and/or the generator 10. The indicator strip 18 has a photochromic material 19 disposed thereon, wherein the photochromic material 19 changes in appearance in proportion to intensity and duration of exposure to the ultraviolet radiation in the UVC range. Indicator strip 18 may optionally include a substrate (not shown) for holding the photochromic material 19.

The indicator strip 18 may be releasably or permanently mounted to any desired surface by any suitable means. However, in the preferred embodiment, strip 18 may be self-adhesive, having a pre-gummed rear surface which is revealed by peeling off a backing strip (not shown).

It is to be understood that the photochromic material 19 may comprise any photochromic material which functions suitably as described herein. Some examples of suitable types of photochromic compounds are found in U.S. Pat. No. 5,581,090 and U.S. Pat. No. 5,436,115, the disclosure of which are incorporated by reference herein in their entirety. An indicator strip 18 according to the present invention may be made using a photochromic material 19 which becomes more or less opaque when exposed to UV radiation. An example of such a material is disclosed in U.S. Pat. No. 4,788,433, the disclosure of which is incorporated by reference herein in its entirety. Some such materials are opaque under normal conditions and become transparent after exposure to a predetermined amount of UVC radiation. An indicator strip 18 in accordance with the present invention may be made by applying such a material over a colored backing material such that exposure to a predetermined level of radiation reveals the colored backing to give a visual indication. In the preferred embodiment, photochromic material 19 is selected from the group consisting of spiropyrans, spirooxazines, and mixtures thereof.

An indicator strip 18 according to the present invention may be constructed such that the entire indicator changes color uniformly when exposed to a predetermined amount of UVC radiation. For example, the photochromic material 19 used in the present invention may be of a type which changes its appearance gradually as the level of exposure to UV radiation increases. In such a case, the degree of change in appearance can be used to provide an indication of how much UV radiation has been received. Alternatively, the photochromic material may be formulated to change appearance abruptly when a desired threshold level of radiation has been received.

Indicator strip 18 according to the present invention may also be constructed such that the indicator may have two or more areas on its surface which change color at different levels of exposure. For example, an area at a first end of the indicator strip 18 may change color after a low level of exposure, followed by a central area of the indicator strip 18 after a medium level of exposure, followed by an area at a second end of the indicator strip 18 after a high level of exposure. The color change of the three areas on the indicator strip 18 may correspond to required levels of exposure for effective sterilization of different quantities of liquid or quantities having different contamination levels.

The photochromic material 19 of the present invention is preferably optimized to react solely or primarily to radiation in the UVC range. This helps to ensure that the material 19 indicates essentially only exposure to wavelengths that are useful for sterilization, and not other wavelengths such as UVA or UVB which are predominant in natural sunlight. One such method is to cover the indicator strip 18 with an additional layer of material that is transparent to UVC, but opaque to UVA and UVB. As such, the indicator strip 18 may optionally include a filtering material 27 (shown in phantom in FIG. 4) disposed over a layer of photochromic material 19, a layer of the filtering material 27 adapted to filter out ultraviolet radiation in the UVA and UVB bands.

An indicator strip 18 according to the present invention may be waterproof and/or may be made so by coating with a layer of material transparent to UVC and waterproof, in order to facilitate immersion in a liquid 14 to be sterilized.

Indicator strip 18 may be a single use item; or alternately, it may be a reusable item. If strip 18 is a single use item, the photochromic material 19 of indicator 18 may be formulated to undergo an irreversible appearance change when exposed to UVC radiation, in which case the indicator strip 18 is disposed of after a single use. Such single-use indicators should be stored in an opaque (or otherwise UV radiation-blocking) container 20 (see FIG. 3) to prevent premature, inadvertent exposure to ambient or stray ultraviolet radiation such as sunlight or fluorescent lighting.

Alternatively, if strip 18 is a reusable item, the photochromic material 19 has an unexposed appearance to which the photochromic material 19 reverts upon cessation of exposure to the ultraviolet radiation in the UVC range; ie. indicator strip 18 is made using a photochromic material 19 which undergoes a reversible appearance change. Such a photochromic material 19 may return to its original unexposed state over time when the exposure has ceased, so that it could be reused many times. If such a reusable strip 18 is used, the user should observe the appearance of strip 18 during or immediately after terminating exposure to the UVC radiation, before its appearance begins to revert to the pre-exposure state.

The monitoring means may further optionally comprise a pre-printed reference card 22 having a plurality of distinctly colored areas and/or opacity reference areas 30 wherein each of the plurality of colored/opacity areas 30 matches the appearance of the photochromic material 19 after varied amounts of exposure to UVC radiation. To accurately determine whether sufficient UV exposure to adequately sterilize a certain material 14 has taken place, the user may compare the post-exposure appearance of the indicator strip 18 with the reference card 22 (see FIGS. 3 and 4). Each of the plurality of colored areas 30 is permanently colored to match the appearance of the indicator strip 18 after a predetermined amount of UVC exposure has taken place. If reference card 22 is to be used with an indicator strip 18 which changes its appearance gradually as exposure increases, the reference card 22 may have several areas of different color corresponding to the appearance of the indicator strip 18 at different levels of exposure (eg. the color coded chart/colored areas 30 may vary by hue). It is to be understood, however, that reference card 22 may have any number of colored areas 30, including just one area 30.

Figure 3:
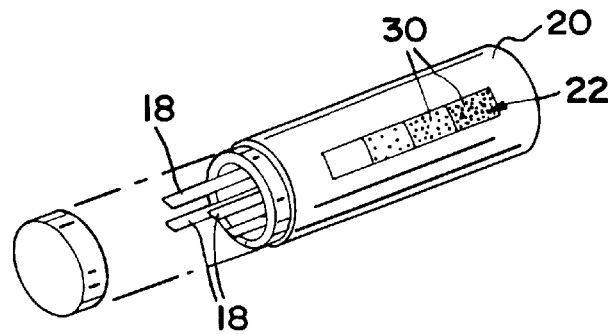
FIG. 3 is a perspective view of a storage container holding a plurality of sterilization indicator strips and a reference card affixed to the outer surface of the container.
Figure 4:
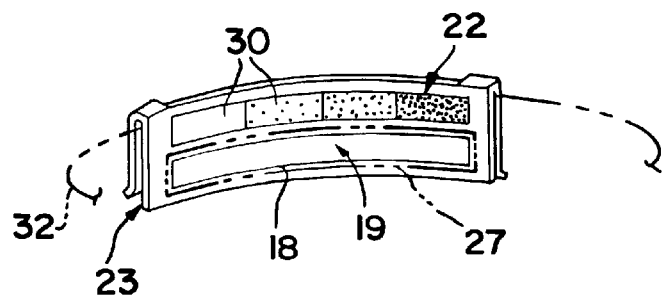
FIG. 4 is a perspective view of a sterilization indicator and reference card mounted together on a single substrate.

In FIG. 3, reference card 22 is shown affixed to the outer surface of container 20. Alternatively, a reference card 22 may be stored inside container 20 along with the supply of indicator strips 18. Indicator strip 18 and reference card 22 may also be mounted together on a carrier 23, as seen in FIG. 4, which is placed on the UV source 10, 10', in or on the material 14 being sterilized, or in or on the reservoir 12 holding the sample. Although carrier 23 is shown suitably shaped and sized for placement over an upper edge (in phantom) of reservoir wall 32, it is to be understood that carrier 23 may be of any desired shape and/or size.

Although reference card 22 may be used, it is also to be understood that a level of UV radiation suitable for sterilization may be made discernable and/or self evident upon visual inspection of the indicator strip 18 itself.

The monitoring means preferably detects UV radiation in the UVC band, namely from a wavelength of about 100 nm to about 290 nm, which wavelength range will generally kill bacteria and other biological contaminants. The UVC radiation detected is more preferably in the wavelength range from about 200 nm to 290 nm.

Figure 5:
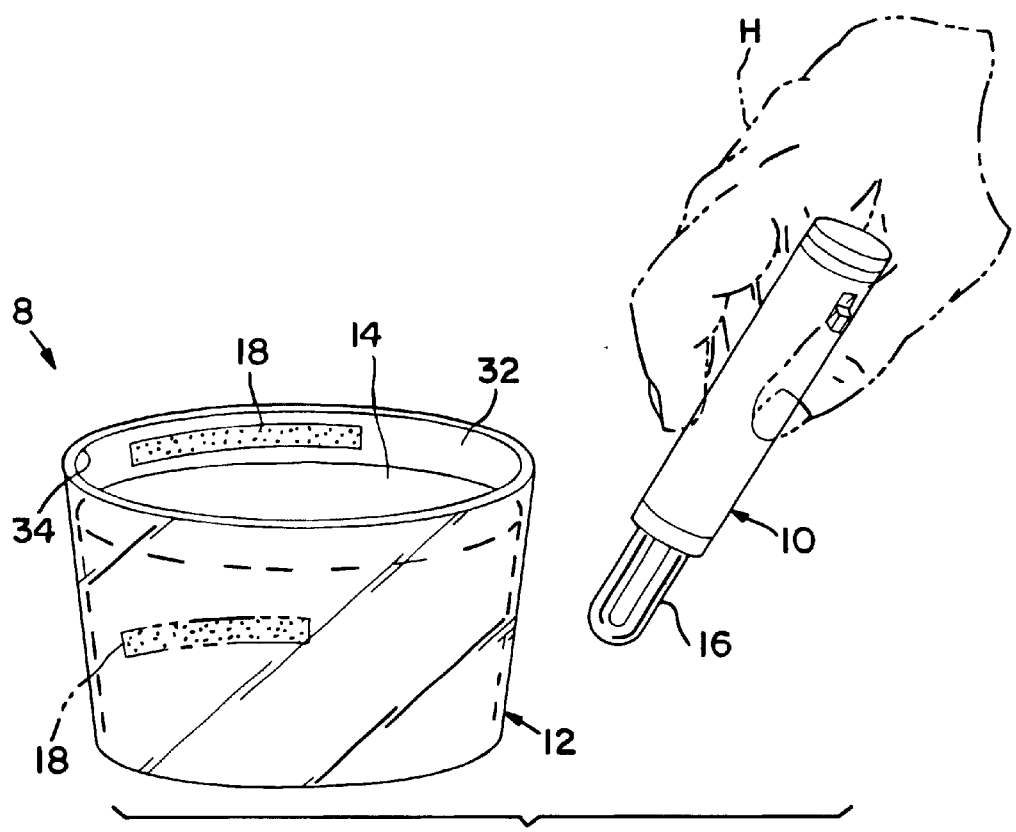
FIG. 5 is a perspective view of a sterilization indicator according to the present invention showing the UV generator operatively positioned by a hand (in phantom) outside the reservoir.

Apparatus 8 of the present invention may further comprise a reservoir 12 for holding a predetermined volume of the material 14, eg. a sterilizable fluid (such as water) as shown in FIGS. 1 and 5. As shown in FIG. 1, apparatus 8 and specifically reservoir 12 may comprise at least one wall 32 adapted to be adjacent the desired material 14. Indicator strip 18 may be permanently or releasably mounted on wall 32 and/or on UV generator 10. Although not shown, the strip 18 may optionally be disposed on bulb 16 of the UV radiation generator 10.

As shown in FIG. 1, the ultraviolet radiation generator 10 may be operatively disposed within the reservoir 12. Alternately, as shown in FIG. 5, the ultraviolet radiation generator 10 may be operatively disposed outside the reservoir 12, assuming reservoir 12 is transparent to UV radiation. If reservoir 12 is not transparent to UV radiation, material 14 may be exposed to the UV radiation from outside reservoir 12 through access aperture 34 (described hereinbelow). In either case, material 14 may be exposed to sufficient UVC radiation in order to sterilize material 14.

Reservoir 12, 12' may define an access aperture 34, 34' for selectively inserting the indicator strip 18 and/or the ultraviolet radiation generator 10 within the reservoir, and/or for allowing UV radiation to pass from outside reservoir 12, 12' thereinto. The reservoir 12 shown in FIGS. 1 and 5 is suitable for sterilizing a material 14 via a batch process, where a quantity of, for example a sterilizable fluid 14, such as water, is placed in the reservoir 12, and exposed to UV radiation in the UVC range. After the fluid 14 has been exposed for a sufficient time, as indicated by the indicator strip 18, the fluid 14 may be replaced by a new quantity of fluid to be sterilized.

Figure 2:
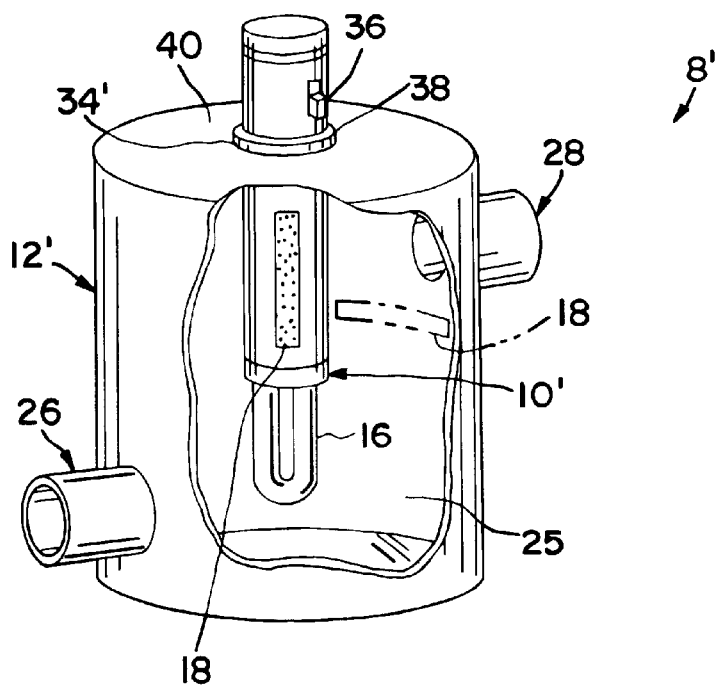
FIG. 2 is a cutaway perspective view of an alternate embodiment of the sterilization apparatus of the present invention, showing the indicator strip in phantom on a flow-through reservoir, and showing the indicator strip on the UV generator.

In an alternate embodiment as shown in FIG. 2, the reservoir 12' further comprises an inlet port 26 and an outlet port 28. In this embodiment, the apparatus 8' sterilizes the fluid 14 in a continuous, flow-through process. Reservoir 12' comprises a sterilization chamber 25. UV generator 10' may optionally include a shoulder 38 sized so as to rest on the upper surface 40 of reservoir 12' adjacent access aperture 34'. It is to be understood that in this embodiment also, the ultraviolet radiation generator 10' may be operatively disposed outside the reservoir 12', assuming reservoir 12' is transparent to UV radiation. If reservoir 12' is not transparent to UV radiation, material 14 may be exposed to the UV radiation from outside reservoir 12' through access aperture 34'.

Apparatus 8' may be used to sterilize liquids or gases (a non-limitative example of which is air) which are pumped or otherwise forced into chamber 25 through inlet port 26 and exit chamber 25 through outlet port 28. The flow rate of the liquids or gases being treated tnrough chamber 25 is controlled to ensure that each incremental amount of material to be sterilized 14 spends sufficient time within the chamber to receive a sterilizing dose of UV radiation from UV radiation generator 10'.

It is to be understood that chamber 25 may be of any desired configuration, as desired and/or necessary, including but not limited to round, rectangular or the like. Further, it is contemplated as being within the purview of the present invention that chamber 25 may itself be existing or new duct work accommodating, for example, flow of air in heating/cooling applications. Indicator strip 18 may then be placed in any operative area as set forth herein, for example within the duct work and/or on the lens of the UVC lamp 16.

As shown, indicator strip 18 may be permanently or releasably mounted on UV radiation generator 10'; and/or indicator strip 18 may be permanently or releasably mounted to the interior surface of chamber 25. In either of these mounting positions, indicator strip 18 is exposed to UV radiation from generator 10' and changes appearance as described above.

It is to be understood that, in any of the embodiments described herein, if reservoir 12, 12' is transparent to UV radiation, indicator strip 18 may be permanently or releasably mounted on an exterior surface of reservoir 12, 12'. As such, it is believed readily is apparent that indicator strip 18 may be, but is by no means required to be disposed within the sterilizable fluid 14.

An indicator strip 18 according to the invention may also be used to verify the UV sterilization of a surface of solid and/or hollow objects, such as, for example, medical instruments. For this type of use, indicator strip 18 is merely placed on or near the object to be sterilized, and its appearance is examined after exposure in the manner described above.

A method for sterilizing a desired material 14, such as for example an aqueous solution (eg. water) according to the present invention comprises the steps of: directing ultraviolet radiation (UV) in the range from about 200 nm to about 290 nm toward the aqueous solution; and monitoring the aqueous solution to detect an amount of cumulative exposure thereto by the ultraviolet radiation. It is to be understood that all of the alternate embodiments and advantages connected therewith described hereinabove with regard to apparatus 8, 8' are suitably usable in the method of the present invention.

Figure 6:
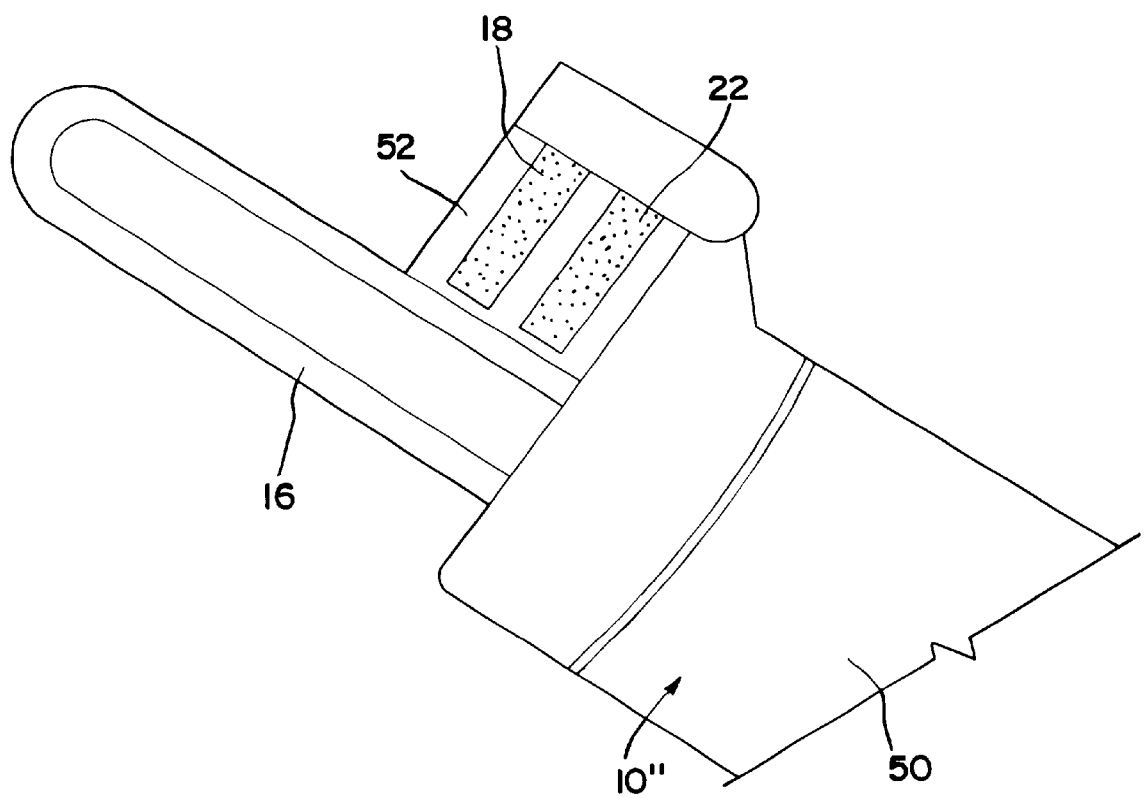
FIG. 6 is a perspective view of a preferred embodiment of the apparatus of the present invention, showing the sterilization indicator mounted on the UV generator housing, and also showing a reference card mounted on the UV generator housing.

Referring now to FIG. 6, there is shown a preferred embodiment of the apparatus of the present invention. UV generator 10" includes a housing 50 having a lip 52 extending outwardly therefrom and operatively spaced from the bulb 16. It is preferred that lip 52 have a slightly concave orientation relative to bulb 16.

When the material to be sterilized is a liquid, it is preferred that the indicator strip 18 be located in a direct line of sight with the UVC source. It is also preferred that the indicator strip 18 and the UVC source be contained within the liquid 14 (see, for example, FIG. 1 and strip 18 in phantom within the liquid). The indicator strip 18 provides a direct linear color change as to the distance and time exposed to the UVC source. Without being bound to any theory, it is believed that (when reservoir 12, 12' is formed from glass) the UVC energy is contained in the reservoir 12, 12' by reflection of the energy off the glass reservoir surfaces and the top surface of the liquid 14, eg. water. The UVC energy bounces around in the water mass until it dissipates.

The apparatus 8, 8' and method of the present invention provides many advantages. One such advantage is that photochromic material 19 of the indicator strip 18 is formulated to undergo a specific and easily identifiable appearance change when it has absorbed an amount of UVC radiation which corresponds to the minimum amount of UVC exposure to adequately sterilize the quantity of fluid 14 held in reservoir 12, 12'. As such, indicator strip 18 thereby provides the user of the radiation generator 10, 10' with a visual indication of the amount of UVC radiation to which fluid 14 has been exposed, and consequently whether the device has been operated for a length of time sufficient to make the fluid safe for drinking, if such is the desired end use of the fluid 14.

While preferred embodiments, forms and arrangements of parts of the invention have been described in detail, it will be apparent to those skilled in the art that the disclosed embodiments may be modified. Therefore, the foregoing description is to be considered exemplary rather than limiting, and the true scope of the invention is that defined in the following claims.

What is claimed is:

1. A handheld apparatus for sterilizing a desired material retained within a container, the apparatus comprising:
    a UV generator including:
        a UV generating bulb, the UV generating bulb being structurally configured for at least partial submersion into the desired material, the UV generating bulb being capable of generating light in the UVC range in the submersed orientation; and
        a switch capable of selectively activating the UV generating bulb; and
    means for directly monitoring the desired material, to, in turn, detect an amount of cumulative exposure of light in the UVC range from the UV generator through the desired material wherein the UV generator further includes:
        a housing associated with the UV generating bulb, the housing having a lip member associated therewith, the lip member extending outwardly and operatively spaced apart from the UV generating bulb;
    the direct monitoring means further includes:
        an indicator strip; and
        a photochromic material disposed thereon, wherein the photochromic material changes in appearance in proportion to at least one of intensity and duration of exposure to light in the UVC range; and
        wherein the indicator strip is positioned on the lip of the housing so as to be directly exposed to the UV generating bulb.

2. The handheld apparatus of claim 1, wherein the indicator strip is releasably associated with the housing.

3. The handheld apparatus of claim 1, wherein the lip member includes a concave orientation relative to the UV generating bulb.

4. The handheld apparatus of claim 1, wherein the direct monitoring means comprises:
    an indicator strip; and
    a photochromic material disposed thereon, wherein the photochromic material changes in appearance in proportion to at least one of intensity and duration of exposure to light in the UVC range.

* * * * *